US012779167B2

(12) United States Patent
Zeis

(10) Patent No.: US 12,779,167 B2
(45) Date of Patent: Nov. 3, 2026

(54) TAPE ASSEMBLY FOR A SMART CATHETER

(71) Applicant: FREUDENBERG MEDICAL, LLC, Beverly, MA (US)

(72) Inventor: Timothy S. Zeis, Charlestown, IN (US)

(73) Assignee: FREUDENBERG MEDICAL, LLC

( * ) Notice: Subject to any disclaimer, the term of this patent is extended or adjusted under 35 U.S.C. 154(b) by 252 days.

(21) Appl. No.: 18/479,930

(22) Filed: Oct. 3, 2023

(65) Prior Publication Data

US 2024/0115832 A1 Apr. 11, 2024

Related U.S. Application Data

(60) Provisional application No. 63/448,005, filed on Feb. 24, 2023, provisional application No. 63/414,938, filed on Oct. 11, 2022.

(51) Int. Cl.

*A61M 25/00* (2006.01)
*A61B 5/00* (2006.01)
*H05K 3/20* (2006.01)

(52) U.S. Cl.

CPC ....... *A61M 25/0009* (2013.01); *A61B 5/6852* (2013.01); *A61M 25/005* (2013.01); *H05K 3/20* (2013.01)

(58) Field of Classification Search

CPC ............ A61M 25/0009; A61M 25/005; A61M 25/0012; A61B 5/6852; H05K 3/20; H05K 2201/09236; H05K 2201/09263; H05K 2203/013; H05K 3/025; H05K 2203/0156; H05K 1/118; H05K 2203/1545

See application file for complete search history.

(56) References Cited

U.S. PATENT DOCUMENTS 3,655,496 A * 4/1972 Ettre ...................... H05K 3/207 257/E21.534
3,785,895 A * 1/1974 Ettre ...................... H05K 3/207 257/E21.534
2010/0228202 A1 9/2010 O'Dea et al.
2015/0366508 A1 12/2015 Chou et al.
2021/0076988 A1 3/2021 Wang et al.
2021/0316113 A1 10/2021 Niederhauser et al.

FOREIGN PATENT DOCUMENTS

EP 0148601 A2 * 7/1985 ............. H05K 3/046
EP 1639353 B1 6/2018
EP 3406193 B1 12/2021
WO WO-2009001327 A2 * 12/2008 ........ A61M 25/0013

* cited by examiner

*Primary Examiner* — Patricia L. Nordmeyer
(74) *Attorney, Agent, or Firm* — Dickinson Wright PLLC

(57) ABSTRACT

A tape assembly for transferring a circuit onto a catheter shaft includes a removable transfer media layer and a circuit assembly disposed in releasably bonded relationship with the transfer media layer. The circuit assembly includes a conductive circuit layer having at least one circuit, and a dielectric layer disposed in overlaying relationship with the conductive circuit layer. The circuit assembly can also include an adhesive layer disposed in overlaying relationship with the dielectric layer and a seal layer disposed in sandwiched relationship between the transfer media layer and the conductive circuit layer. The transfer media layer provides support for the circuit assembly during transfer to the catheter shaft, and is removable from the circuit assembly after application to the catheter shaft to provide a reduced profile for the resultant smart catheter shaft.

12 Claims, 7 Drawing Sheets

TAPE ASSEMBLY FOR A SMART CATHETER

CROSS REFERENCE TO RELATED APPLICATIONS

The subject application is related to U.S. Provisional Patent Application Ser. No. 63/414,938 filed on Oct. 11, 2022 and U.S. Provisional Patent Application Ser. No. 63/448,005 filed on Feb. 24, 2023, the entire disclosures of which are incorporated herein by reference.

BACKGROUND OF THE INVENTION

1. Field of the Invention

The present disclosure relates generally to medical devices and procedures. In particular, the present disclosure relates to circuits for a smart catheter.

2. Description of the Prior Art

This section provides background information related to the present disclosure which is not necessarily prior art.

A catheter is a medical instrument for use in accessing an interior of a patient's body with a distal tip during a medical procedure. The catheter can include at least one working component, such as a fluid channel, a working channel, and/or an electronics cable, which extend along the catheter and terminate at or adjacent the distal tip. There is a growing trend in the industry to also integrate circuits into the catheter shaft, thereby providing intelligence to the catheter (i.e., a "smart catheter"). Smart catheters need to articulate and steer the distal tip through the body to reach their target destination, with tight bends being required. The catheter shaft will also bend as it pushes through the tortious path of the human body, which causes compression and expansion points on the catheter shaft. The more the catheter shaft bends, the greater the effect.

The prior art circuits are commonly integrated into the catheter shaft by flowing a flexible circuit 37 embedded in a stretchable thermoplastic polymer encasement (See e.g., element 36 in FIG. 2D) or a less stretchable polyamide film, each of which functions as the substrate for the circuit. This substrate is required and must be present to provide structural support for the small fragile electrical pathways of the prior art circuit 37. However, the presence of this structural support for the circuit has significant drawbacks. For example, because polyimide film does not have sufficient flexibility to accommodate the required compression and expansion encountered in a catheter shaft application, use of polyimide film as the support is limited on how and at what lengths it can be applied. On the other hand, use of the stretchable thermoplastic polymer adds significant thickness to the catheter shaft. More specifically, since stretchable materials are less rigid, they are less suitable as a structure, and more thickness must be added to compensate for this drawback. With reference to FIG. 2D, in the case of a smart catheter application, the added thermoplastic polymer encasement 36 (a 0.20 mm thickness being common) required to embed the circuit 37 can increase a diameter of the catheter shaft by as much as twenty times the thickness of the circuit itself (which may only be 0.01 mm), which is functionally detrimental to the final diameter of the catheter product. In addition, because the prior art circuit 37 is embedded in the polymer encasement 36, when the polymer melts during the reflow process, the circuits begin to move around the liquefying polymer, creating potential for the circuits to short out on one another or on the braid layer. In summary, in these prior art cases, the substrate must be strong enough to support the circuit structure, and after the circuit is transferred, the polymer encasement 36 support structure (e.g., the polyimide film or the thermoplastic polymer) becomes part of the catheter structure itself. This negatively impacts the size and flexibility of the resultant smart catheter. Accordingly, there remains a continuing need for improved ways of incorporating a circuit into the catheter shaft during manufacture of the smart catheter.

SUMMARY OF THE INVENTION

This section provides a general summary of the disclosure and is not intended to be a comprehensive disclosure of its full scope, aspects, objectives, and/or all of its features.

A tape assembly for transferring at least one circuit onto a catheter shaft includes a removable transfer media layer extending between a first end and a second end. A circuit assembly is disposed in overlaying and releasably bonded relationship with the removable transfer media layer between the first and second ends, and includes a conductive circuit layer having at least one circuit. The removable transfer media layer provides temporary structural support for the circuit assembly until the circuit assembly is transferred to become part of the catheter shaft. Once the transfer is complete, the removable transfer media layer is removed and discarded, leaving only the circuit assembly behind, in secured relationship with the catheter shaft.

Relatedly, a method of manufacturing a smart catheter includes providing a catheter shaft, and providing a tape assembly including a removable transfer media layer and a circuit assembly having a conductive circuit layer. The method proceeds by applying the tape assembly to the catheter shaft to dispose the circuit assembly in overlaying relationship with the catheter shaft, and then removing the removable transfer media layer from the circuit assembly to leave the circuit assembly applied to the catheter shaft.

The tape assembly provides a means of manufacturing a better, more reliable smart catheter shaft. More specifically, the transfer of the circuit assembly directly onto the catheter shaft, without the need of including a support structure (e.g., a thermoplastic polymer encasement 36) as part of the permanent structure of the catheter shaft, keeps the catheter's profile (i.e., diameter) at a minimum (See, e.g., a comparison of FIG. 2B illustrating the catheter shaft prior to transfer of the circuit assembly to FIG. 2C illustrating the catheter shaft with the transferred circuit assembly after removal of the transfer media layer) while allowing for the best flexibility possible. A lower profile also helps to keep the circuit positionally stable with minimal chance of moving, which could cause shorts and breaks. For comparison, if the circuit present in the conductive circuit layer was encased in a structural thermoplastic encasement prior to the transfer taking place, as required by the prior art, the thermoplastic encasing the circuit would need to be heated to a liquid state during the transfer to get the thermoplastic and circuit to stick to the catheter shaft, during which time the circuit could shift and move in the melt.

BRIEF DESCRIPTION OF THE DRAWINGS

Other aspects and advantages of the present disclosure will be readily appreciated, as the same becomes better understood by reference to the following detailed description when considered in connection with the accompanying drawings wherein.

DESCRIPTION OF THE ENABLING EMBODIMENTS

Example embodiments will now be described more fully with reference to the accompanying drawings. The example embodiments are provided so that this disclosure will be thorough and fully convey the scope to those skilled in the art. Numerous specific details are set forth such as examples of specific components, devices, mechanisms, assemblies and methods to provide a thorough understanding of various embodiments of the present disclosure. It will be apparent to those skilled in the art that specific details need not be employed, that example embodiments may be embodied in many different forms, and that neither should be construed to limit the scope of the disclosure. With this in mind, the present disclosure is generally directed to a tape assembly 10 for applying a circuit 20 to a catheter shaft 30 during manufacture of a smart catheter.

Figure 6A:
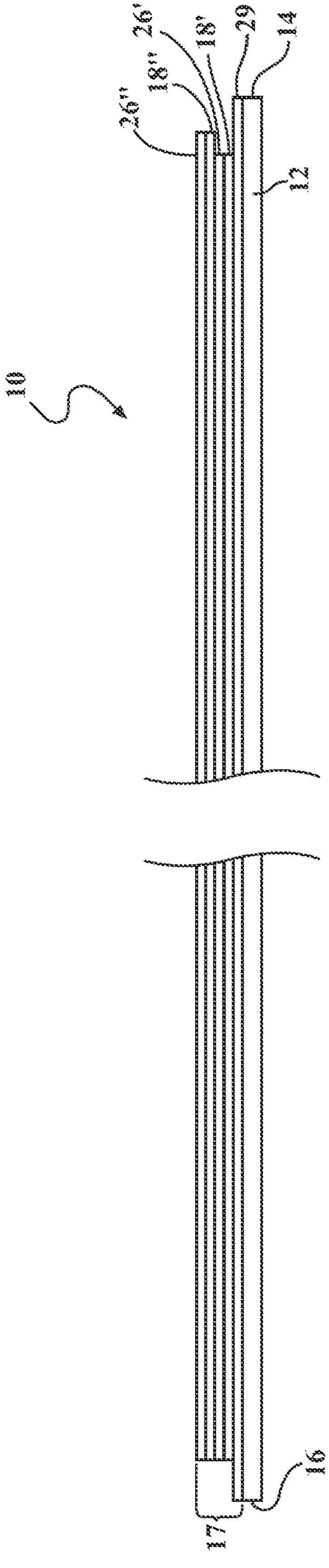
FIG. 6A is a side view of the tape assembly constructed in accordance with a third embodiment and illustrating the circuit assembly including a plurality of conductive circuit layers and a plurality of dielectric layers disposed in alternating stacked relationship with one another.
Figure 6B:
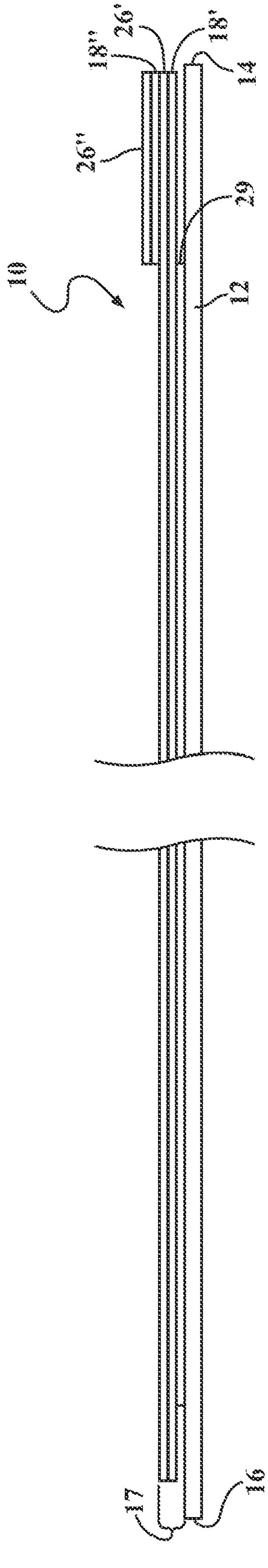
FIG. 6B is a side view of the tape assembly illustrating an alternative arrangement of the third embodiment that incorporates more complex circuit patterns in place of the contact pads in the circuit to incorporate further functionality into the circuit assembly.
Figure 7A:
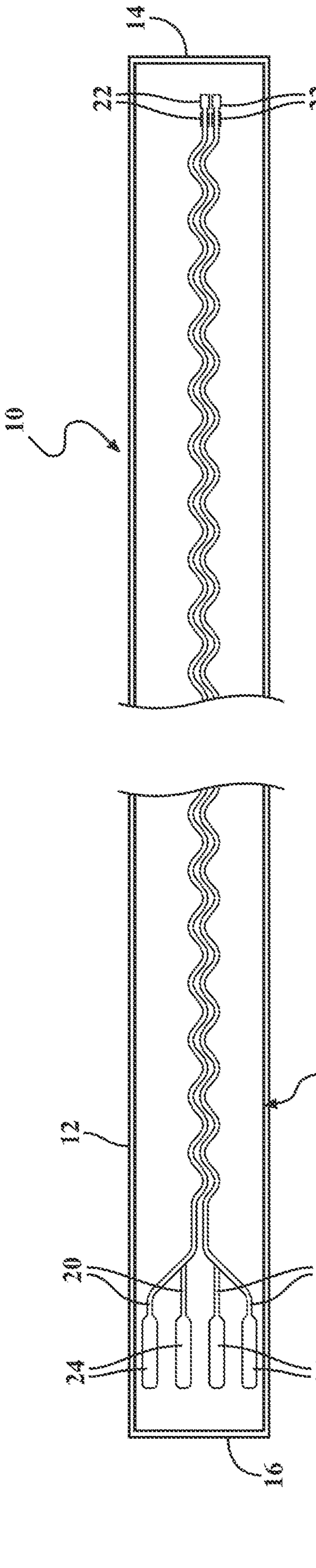
FIG. 7A is a top view of the tape assembly in accordance with any of the aforementioned embodiments to illustrate a different arrangement of the conductive circuit layer of the circuit assembly including a plurality of contact pads disposed at an end of the circuit.
Figure 7B:
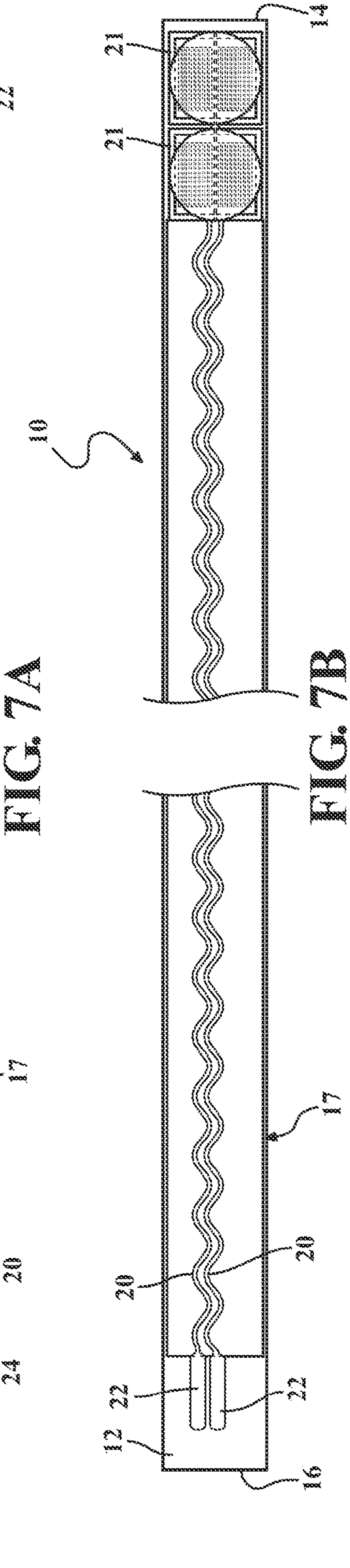
FIG. 7B is a top view of the tape assembly in accordance with any of the aforementioned embodiments to illustrate a different arrangement of the conductive circuit layer of the circuit assembly in which sensors replace the contact pads of the circuit.
Figure 7C:
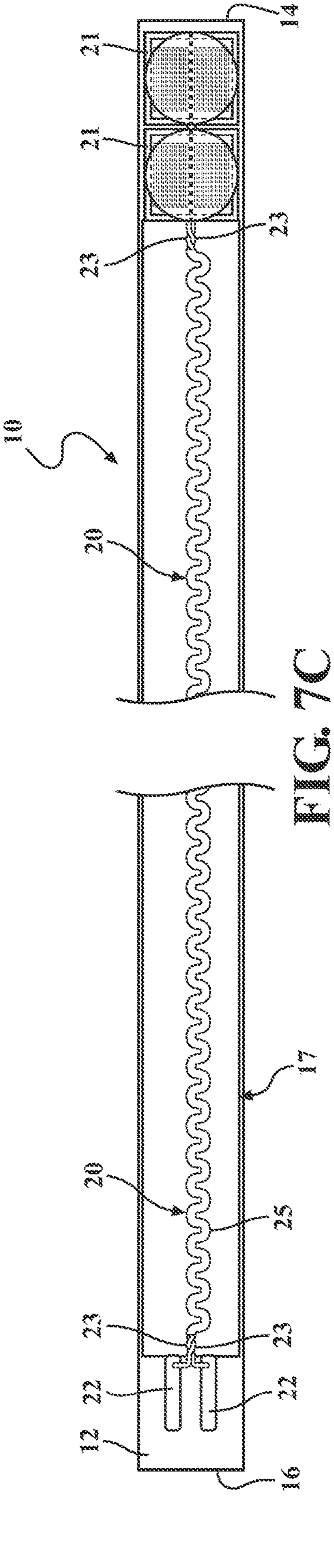
FIG. 7C is a top view of the tape assembly in accordance with any of the aforementioned embodiments to illustrate a different arrangement of the conductive circuit layer of the circuit assembly in which round wires can be incorporated into the circuit as a substitute for a flat conductive metal.

Referring to the Figures, wherein like numerals indicate corresponding parts throughout the several views, the tape assembly 10 is generally shown in FIGS. 1A, 1C and 6A-6B. As best illustrated in FIGS. 1A, 1C and 6A-6B, the tape assembly 10 includes a removable transfer media layer 12 extending between a first end 14 and a second end 16, and a circuit assembly 17 overlaying and removably bonded to the removable transfer media layer 12 between the first and second ends 14, 16. The circuit assembly 17 includes a conductive circuit layer 18 having at least one circuit 20. As best illustrated in FIG. 1B in accordance with an aspect, the at least one circuit 20 of the circuit assembly 17 extends between a first contact pad 22 disposed adjacent the first end 14 of the removable transfer media layer 12 and a second contact pad 24 disposed adjacent the second end 16 of the removable transfer media layer 12. As best illustrated in FIG. 7A, each circuit 30 can include a plurality of contact pads 22, 24 at one of (or both) of the ends 14, 16. Furthermore, as illustrated in FIG. 7C, the circuit 20 can also include at least one sensor 21, or other electrical and electronic components, at one or both of the ends 14, 16 in lieu of the contact pads 22, 24 to incorporate further functionality into the circuit assembly. The at least one circuit 20 is preferably comprised of conductive metal materials, such as copper due to its low cost and high conductivity, but other conductive metal materials such as gold or silver could be utilized without departing from the scope of the subject disclosure. Furthermore, as illustrated in FIG. 7C, the at least one circuit 20 can include a plurality of round twisted wires 23 extending between the contact pads 22, 24 or sensors 21 and encased within a sheath 25 (such as to eliminate or reduce noise generated from the circuit 20) in lieu of the flat conductive metal shown in FIGS. 1A and 7A-7B.

Figure 2A:
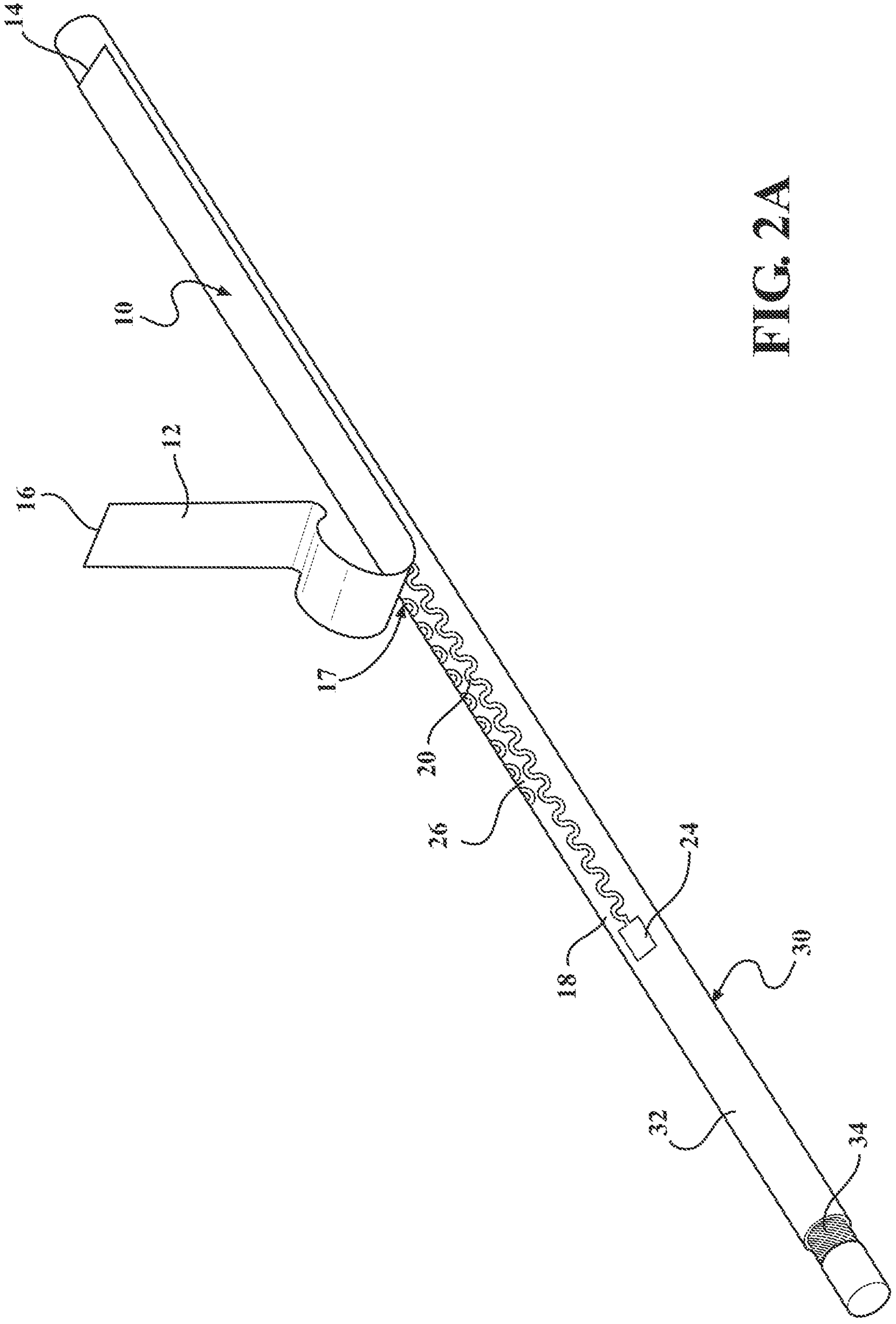
FIG. 2A is a perspective view of a catheter shaft illustrating the tape assembly applied to the catheter shaft after which the removable transfer media layer is removed from the circuit assembly containing the conductive circuit layer, the dielectric coating, the adhesive layer (and the seal layer, if present) to transfer the circuit assembly to the catheter shaft.

The removable transfer media layer 12 can be comprised of any media capable of transferring the circuit assembly 17 to another substrate, such as an outer surface 32 of a catheter shaft 30 as shown in FIG. 2A, without deforming or damaging the circuit assembly 17. In other words, the removable transfer media layer 12 is comprised of a material strong enough to support and maintain an integrity and structure of the thin, circuit assembly 17 including the conductive circuit layer 18 (e.g. a layer that can be on the micron scale) until a transfer to the catheter shaft 30 is made. For example, as will be described in the following more detailed disclosure, the removable transfer media layer 12 in accordance with an aspect can be comprised of a heat transfer tape or heat release tape, each of which releases the circuit assembly 17 from the transferable media layer 12 when a temperature is obtained for a predetermined amount of time. However, the transferable media layer 12 can include other types of releasable media such as heat resistant or other media that does not require application of heat to effectuate a transfer, such as low adhesion tape, without departing from the subject disclosure.

Figure 2C:
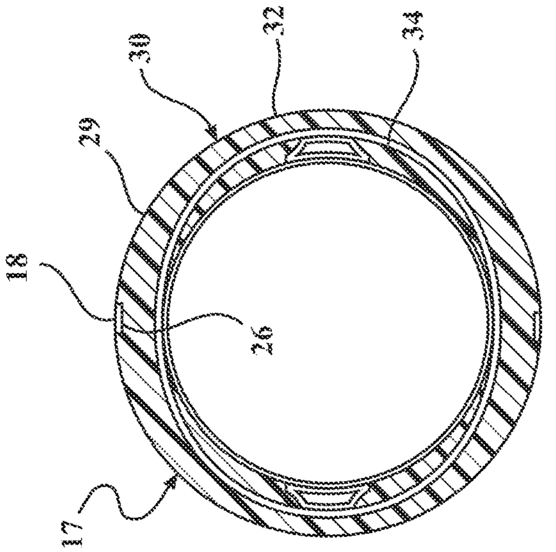
FIG. 2C is a cross-sectional view of the catheter shaft after the circuit assembly is transferred to the catheter shaft and the removable transfer media layer is removed to illustrate the seal layer overlaying and protecting the conductive circuit layer from an environment of the catheter shaft and the dielectric coating protecting the conductive circuit layer from an outer surface and/or a braid layer on the catheter shaft.
Figure 2D:
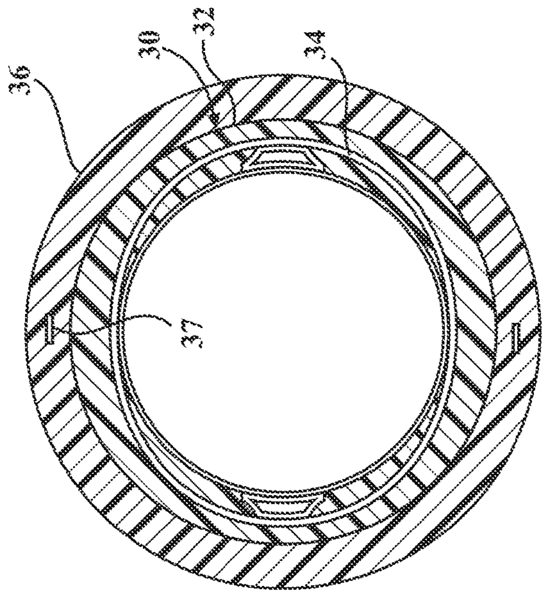
FIG. 2D PRIOR ART
FIG. 2D is a cross-sectional view of the catheter shaft illustrating a prior art approach of embedding the circuit in a structural thermoplastic encasement.

In any arrangement, the removable transfer media layer 12 provides temporary structural support for the circuit assembly 17 until transferred to become part of the catheter shaft 30. In other words, the removable transfer media layer provides structural support before and during the transfer of the circuit assembly 17. As will be explained in more detail below, once the transfer is complete, the removable transfer media layer 12 can be removed and discarded leaving only the circuit assembly 17 behind. And since the circuit assembly 17 does not need to provide structure support on its own, much of the materials used to build the circuit assembly 17 can be eliminated or ultra-thin, measuring only microns, resulting in a smart catheter with a circuit 20 having a smaller diameter relative to the prior art (See FIG. 2C compared to FIG. 2D).

Figure 2B:
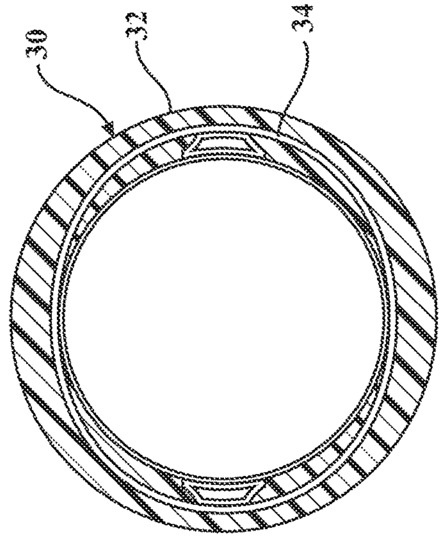
FIG. 2B is a cross-sectional view of the catheter shaft prior to application of the circuit assembly.

As further illustrated in Figures IA, 1C and 6A-6B, the circuit assembly 17 is preferably multi-layered and additionally includes a dielectric layer 26 disposed in overlaying relationship with the conductive circuit layer 18 to dispose the conductive circuit layer 18 in sandwiched relationship between the dielectric layer 26 and the removable transfer media layer 12. However, in an aspect, the circuit assembly 17 could only be comprised of the conductive circuit layer 18 without departing from the scope of the subject disclosure. The dielectric layer 26, if present, protects the conductive circuit layer 18 if a risk of shorting is a concern, such as when a braid layer 34 is present on the catheter shaft 30 (as shown in FIGS. 2A-B). As illustrated in FIG. 2A, when the tape assembly 10 (and thus the circuit assembly 17) is applied to the catheter shaft 30, the dielectric layer 26 is disposed in overlaying relationship with the conductive circuit layer 18 so that it is facing downwards towards the outer surface 32, and particularly the braid layer 34, of the catheter shaft 30. Thus the dielectric layer 26 helps to ensure that the conductive circuit layer 18 does not contact the exposed braid 34 of the catheter shaft 30 which lies radially inward from and just beneath or along the outer surface 32. In other words, the dielectric layer 26 is disposed fully or in part onto the conductive circuit layer 18 to avoid short circuits, such as when multiple conductor circuit layers are stacked on top of one another (See FIGS. 6A-6B) or when the conductive circuit layer 18 could be unintentionally exposed to other conductive materials, such as the braid layer 34. As illustrated in FIGS. 6A-6B, when a plurality of conductor circuit layers 18', 18" are present, a plurality of dielectric layer 26', 26" are also utilized and can be disposed between each adjacent conductive circuit layer 18', 18" to dispose multiple conductive circuit layers 18', 18" and multiple dielectric layers in stacked relationship with one another 26', 26". For example, a first dielectric layer 26' can be disposed in facing relationship with the outer surface 32 of the catheter shaft 30, followed by a first conductive circuit layer 18', then a second dielectric layer 26", and then a second conductive circuit layer 18", etc. In any arrangement—with single layers or multiple layers, the dielectric layer 26 makes the overall device more robust due to the reduced likelihood of circuit breakage or shorting. However, if the catheter shaft 30 does not have a risk of shorting, the dielectric layer 26 could be omitted without departing from the scope of the subject disclosure.

Figure 1A:
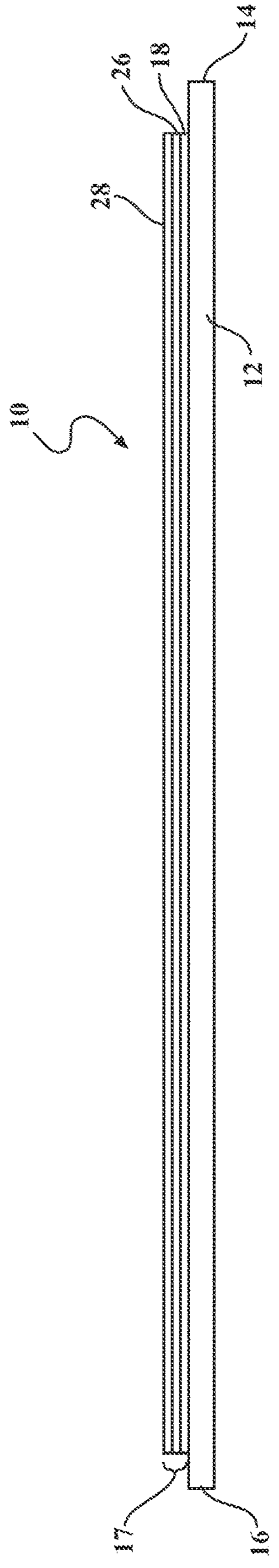
FIG. 1A is a side view of a tape assembly constructed in accordance with a first embodiment and illustrating a removable transfer media layer and a circuit assembly disposed in removably bonded relationship with the removable transfer media layer, the circuit assembly being multi-layered and including a conductive circuit layer, a dielectric layer, and an adhesive layer.
Figure 1B:
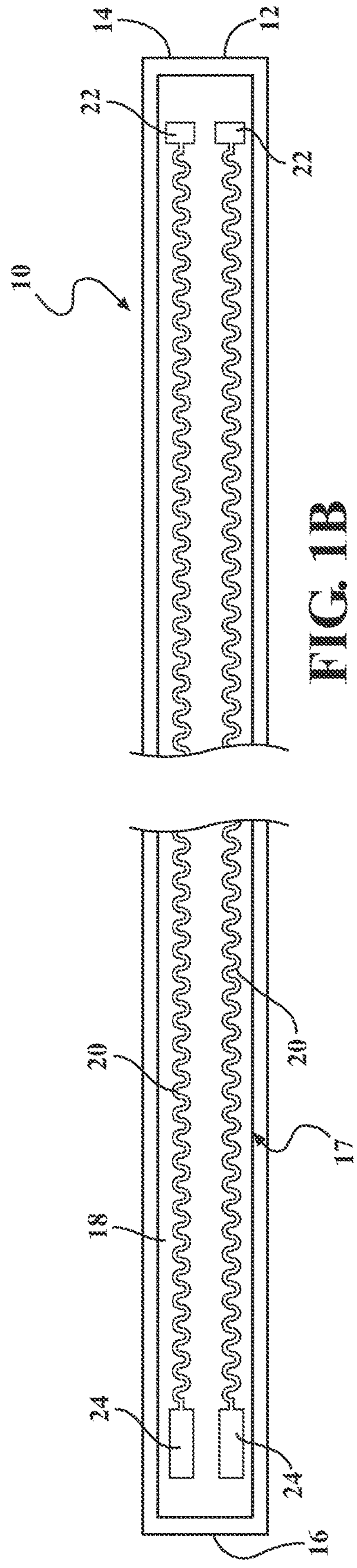
FIG. 1B is a top view of the tape assembly to more clearly illustrate the conductive circuit layer of the circuit assembly.
Figure 1C:
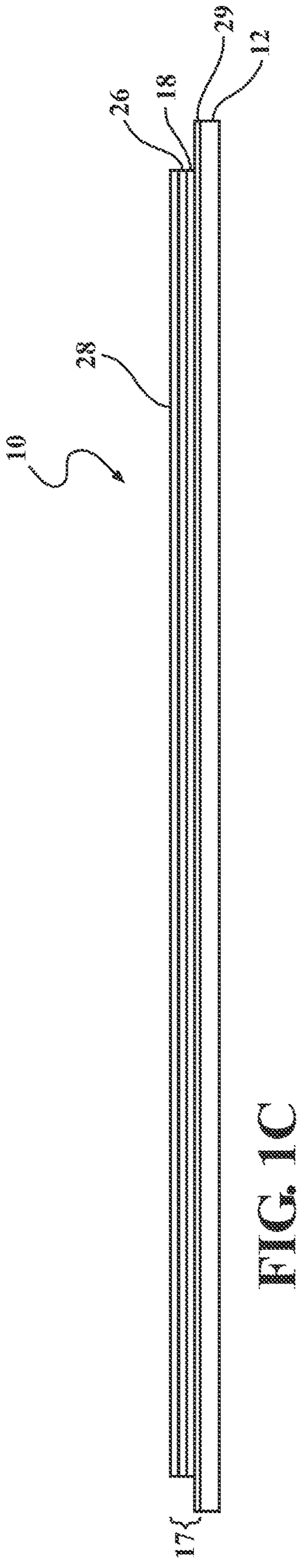
FIG. 1C is a side view of the tape assembly constructed in accordance with a second embodiment and illustrating the circuit assembly additionally including a seal layer disposed in sandwiched relationship between the transferable media layer and the conductive circuit layer.

As illustrated in FIGS. 1A and 1C, the circuit assembly 17 can additionally include an adhesive layer 28 disposed in overlaying relationship with the dielectric layer 26 for use in securing the circuit assembly 17 to the outer surface 32 of the catheter shaft 30. In other words, the adhesive layer 28 assists in bonding the circuit assembly 17 to the catheter shaft 30, or directly to the braid layer 34. Thus, the adhesive layer 28 is placed on the outer most surface of the circuit assembly 17, farthest away from the removable transfer media layer 12. However, in accordance with certain aspects, while the adhesive layer 28 can assist to effectuate transfer and bonding of the circuit assembly 17, the adhesive layer 28 could be removed especially if the circuit assembly 17 is heat transferred or reflowed on the catheter shaft 30, such as will be explained in more detail below. In this situation, with enough heat the circuit assembly 17 will bond mechanically to the thermoplastic catheter shaft 30 as the conductive circuit layer 18 is pushed down into the melted plastic. Thus, in accordance with the subject disclosure, the thermoplastic on the catheter shaft 30 can be used to bond the circuit assembly 17 in lieu of the adhesive layer 28.

As best illustrated in FIG. 2A, in accordance with an aspect, the conductive circuit layer 18 is transferred to the catheter shaft 30 by applying the tape assembly 10 to the outer surface 32 of the catheter shaft 30, disposing the adhesive layer 28 (if present) and the dielectric layer 26 (if present) facing down and sequentially overlaying the outer surface 32 of the catheter shaft 30. Once applied, the transferable media layer 12 is removed from the to tape assembly 10, leaving the circuit assembly 17 secured to the outer surface 32 of the catheter shaft 30, via either the additional adhesive layer 28 or with the other heat transferring or reflowing procedures mentioned above (if adhesive is not present). As illustrated in FIG. 2A, after application of the tape assembly 10, the removable transfer media layer 12 can be peeled away from the circuit assembly 17 and discarded.

As described above, when the tape assembly 10, including the removable transfer media layer 12 and the circuit assembly 17, is applied to the catheter shaft 30, the dielectric layer 26 faces down and overlays the outer surface 32 of the catheter shaft 30. Then, the removable transfer media layer 12 is removed from the circuit assembly 17, which is now part of the construction of the catheter shaft 30, leaving the conductive circuit layer 18 potentially exposed to an environment of the catheter shaft 30. Thus, as illustrated in FIG. 1C and 6A-6B, in an accordance with a second embodiment of the subject disclosure, the circuit assembly 17 can additionally include a seal layer 29 that is disposed in sandwiched relationship between the transferable media layer 12 and the conductive circuit layer 18. When the removable transfer media layer 18 is removed from the circuit assembly 17, the seal layer 29 overlays and protects the conductive circuit layer 18 from the environment (e.g., the human body), providing an efficient way to protect the conductive circuit layer 12 without the need to incorporate additional and costly process steps at a later time to provide this same amount of protection for the conductive circuit layer 18. In a preferred arrangement, the seal layer 29 is a very thin layer of polymer material applied to the conductive circuit layer 18 (such as via lamination, coating, spraying, plating processes, or the like). Accordingly, as best illustrated in FIGS. 2C, this very thin seal layer 29 has a minimal effect on the overall size of the catheter shaft 30, yet still provides protective benefits for the conductive circuit layer 18 without requiring the need to incorporate additional process steps later when manufacturing the catheter shaft 30 to provide this same level of protection. Thus, these reduced processing steps for the catheter shaft 30 lead to lower manufacturing and product costs. While the seal layer 29 is described preferably as a polymer, the seal layer 29 could be any other bio-compatible flexible material without departing from the scope of the subject disclosure.

The tape assembly 10, including the removable transfer media layer 12 and the circuit assembly 17, provides a number of advantages over the prior art methods of incorporating a circuit into the catheter shaft 30 to manufacture a smart catheter. Initially, the removable (and disposable) transferable media layer 12 prevents additional thickness being added to the catheter shaft 30 by way of the application of circuit assembly 17 (since the transfer media layer 12 can be removed after application of the circuit assembly 17 to the catheter shaft 30). This allows for a significant decrease in the overall catheter size (i.e., diameter), which is crucial to minimizing trauma of the patient when the catheter shaft 30 is ultimately in use during a medical procedure. Put another way, the overall thickness of the circuit assembly 17 applied to the catheter shaft 30 (after the transferable media layer 12 is removed) is very thin, providing a smart circuit on the catheter shaft 30, achieving a smaller profile than achievable by the prior art methods of incorporating the circuits via electrical wiring or reflowing the circuit embedded in a structural thermoplastic encasement 36, such as shown in FIG. 2C (subject arrangement) compared to FIG. 2D (prior art).

Furthermore, application of the circuit assembly 17 to an outer surface 32 of the catheter shaft 30 provides a method of manufacturing a smart catheter with reduced cost, reduced assembly time and increased yields over the prior art manufacturing methods. For example, the ability to transfer the circuit assembly 17 directly onto the catheter shaft 30 eliminates the requirement to have the circuit in a structural thermoplastic encasement 36 prior to transfer of the circuit 20 to the catheter shaft (such as required in the prior art illustrated in FIG. 2D), and keeps the circuit 20 stable with minimal chance of movement during transfer to the catheter shaft 30. After transfer of the conductive circuit layer 18 to the catheter shaft 30, the catheter shaft 30 can then move on to other processes required to complete the catheter assembly. For example, it is likely that the contact pads 22, 24 or sensors 21 will need to be exposed, while at the same time the circuit 20 between the contact pads 22, 24 or sensors 21 will need to be covered. One way to accomplish this is by masking what you don't want covered, such as the contact pads 22, 24 or sensors 21, prior to coating the catheter shaft 30 to seal in the areas of the circuit 20 between the contact pads 22, 24 or sensors 21. Methods of coating could be but are not limited to dip, spray and vapor deposition to just name a few. Another possible way to cover the conductive circuit layer 18 is by applying another thin layer of thermoplastic material over the areas that need to be protected against the environment. In cases when the circuit 20 is bonded directly to the braid layer 34, a reflow process can be utilized in which a non-conductive material such as thermoplastic is applied over the braid layer 34 and the circuit 20 which is affixed to the braid layer 34.

Inclusion of the dielectric layer 26 in the circuit assembly 17 prior to transfer of the at least one conductive circuit layer 18 onto the catheter shaft 30 also helps to ensure that the conductive circuit layer 18 will not short out and be damaged during manufacture, such as by contacting the braid layer 34 in the catheter shaft 30. Thus, the dielectric layer 26 allows the conductive circuit layer 18 to be applied to a wide range of outer surfaces, including coils or braid layers. Additionally, use of the removable transfer media layer 12 in the tape assembly 10 keeps the conductive circuit layer 18 stable during transfer to the catheter shaft 30, preventing the conductive circuit layer 18 from floating and making the overall device more robust due to the reduced likelihood of circuit shorting, as well as the elimination of small, fragile wires which are prone to breakage in the prior art designs. Further, presence of the seal layer 29 makes a bond between the transferable media layer 12 and the conductive circuit layer 18 less critical, namely because it eliminates any gaps between these two surfaces which could cause failures in prior art devices while etching in an etchant bath or spray during manufacturing of the circuit assembly. Finally, the tape assembly 10 provides for increased opportunity for attaching customized electrodes or sensors 21 when manufacturing the smart catheter as illustrated in FIGS. 7A-7C.

Figure 3:
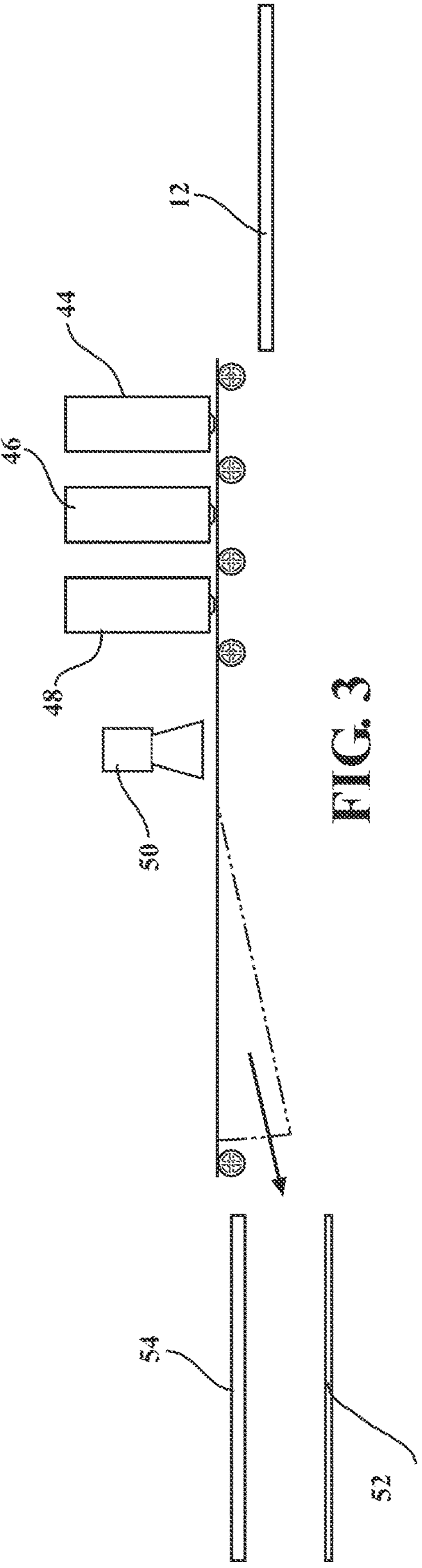
FIG. 3 illustrates a method of manufacturing the tape assembly in accordance with a first exemplary aspect.

As mentioned previously, the conductive circuit layer 18 is comprised of any electronic and/or electrical components used to establish the circuit 20, and could range anywhere from conductive inks to electroplating and chemical milling (also referred to as chemical etching). In certain instances, as illustrated in FIG. 7C, a plurality of twisted wires 23 encased within a sheath 25 may also be a desired approach for the circuit 20, due to the noise-cancelling and shielding effects provided by the sheath 25. Conductive inks might also be the desired approach to manufacture the conductive circuit layer 18 due to their manufacturing simplicity. If conductive inks are used, there are many ways to apply the conductive ink circuit to the transferable media layer 12, such as via screen printing, inkjet, extrusion printing, aerosol jet, electroplating, laser sintering, pulse light sintering, and the like. FIG. 3 illustrates an exemplary method of manufacturing the tape assembly 10 via a conductive ink approach, in which the process begins with pre-bounded sheets of a predetermined length consisting of the removable transfer media layer 12. Each sheet is sequentially passed through a conductive ink print station 44 for applying the conductive circuit layer 18, a dielectric ink print station 46 for applying the dielectric layer 26, and an adhesive ink print station 48 for applying the adhesive layer 28 and completing manufacture of the tape assembly 10. Due to the nature of working with individual pieces, the manufactured sheet of the tape assembly 10 can then be passed through an inspection station 50 to identify rejected product and good product, after which the rejected product is passed to a reject stack 52 and good product is passed to a circuit stack 54.

While manufacturing the conductive circuit layer 18 via conductive inks is suitable, the preferred method of manufacturing is via chemical etching due to the cost, strength characteristics and superior conductivity of 99% copper. The use of chemical etching to manufacture the conductive circuit layer 18 achieves the conductivity needs of conductive circuit layer 18 in the circuit assembly 17 at very thin thicknesses. These thin layers for the conductive circuit layer 18 help to keep an outer diameter of the resultant smart, catheter shaft 30 at a minimum, thus reducing trauma to the patient during a procedure.

There are a variety of ways to approach copper etching, with use of a photo-resist film or photo-resist coating being a commonly used process. However, with reference to FIG. 4, a preferred approach of chemical etching to manufacture the conductive circuit layer 18 is via use of a UV curable dielectric ink. This manufacturing process allows a number of the requisite process steps with use of photo-resist film processing to be eliminated. Additionally, because the circuit assembly 17 on the tape assembly 10 includes a dielectric layer 26, there is no need to remove this dielectric layer 26 after etching has been completed.

Figure 4:
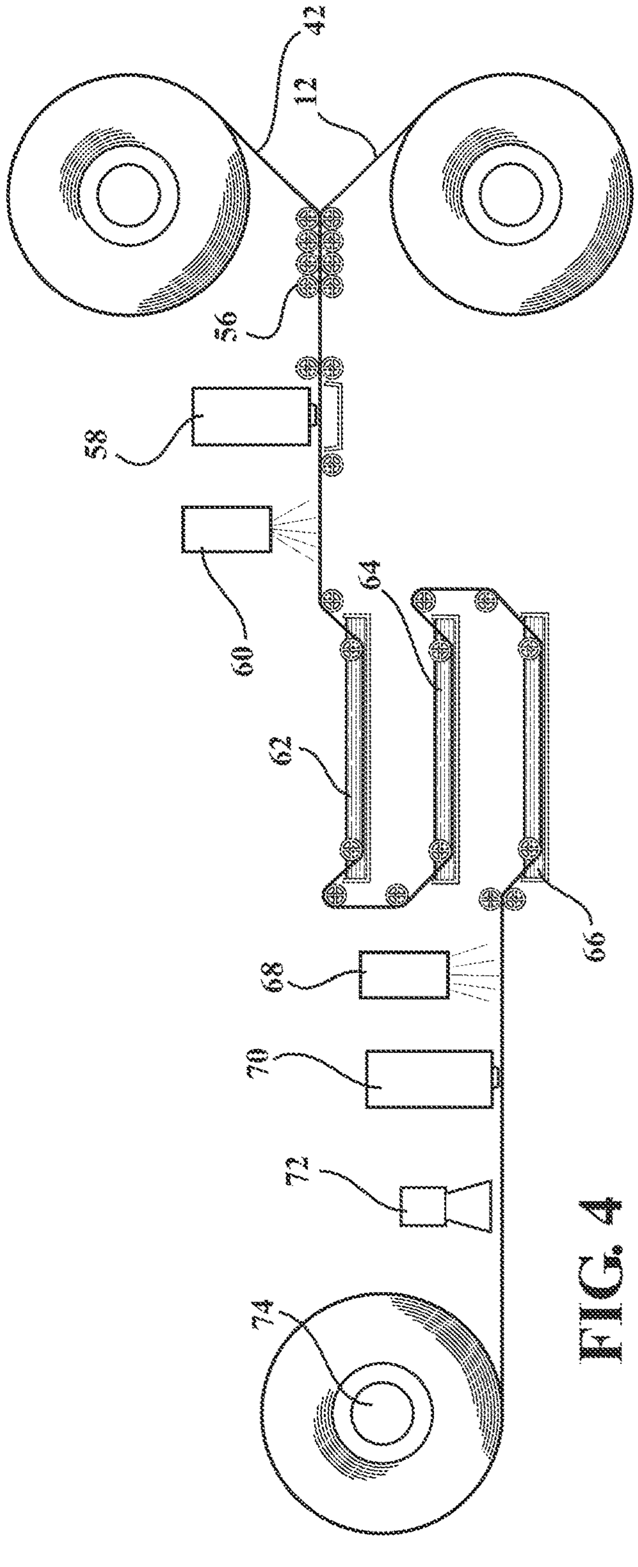
FIG. 4 illustrates a method of manufacturing the tape assembly in accordance with a second exemplary aspect.

With reference to FIG. 4, in accordance with an exemplary aspect, the UV curable dielectric ink manufacturing process begins with the removable transfer media layer 12 being pressed and bound together with clean copper foil 42 using pressure rollers 56. The combined transfer media layer 12 and copper foil 42 then passes through a dielectric ink print station 58 where a desired circuit is printed on the copper foil 42 using UV curable dielectric ink. The printed assembly then passes through a UV curing station 60 followed by an etching cycle sequentially comprised of an etching bath or spray 62, an etchant neutralizing bath or spray 64 and a rinse bath or spray 66 to form the conductive circuit layer 18. When the etched conductive circuit layer 18 comes out of the rinse bath or spray 66, it is then dried in a dry station 68, after which the optional adhesive layer 28 can be applied via an adhesive dispenser 70. The completed tape assembly 10 then passes through an inspection camera 72 after which it is rolled onto a spool 74 and ready for use and application to a catheter shaft 30.

Figure 5:
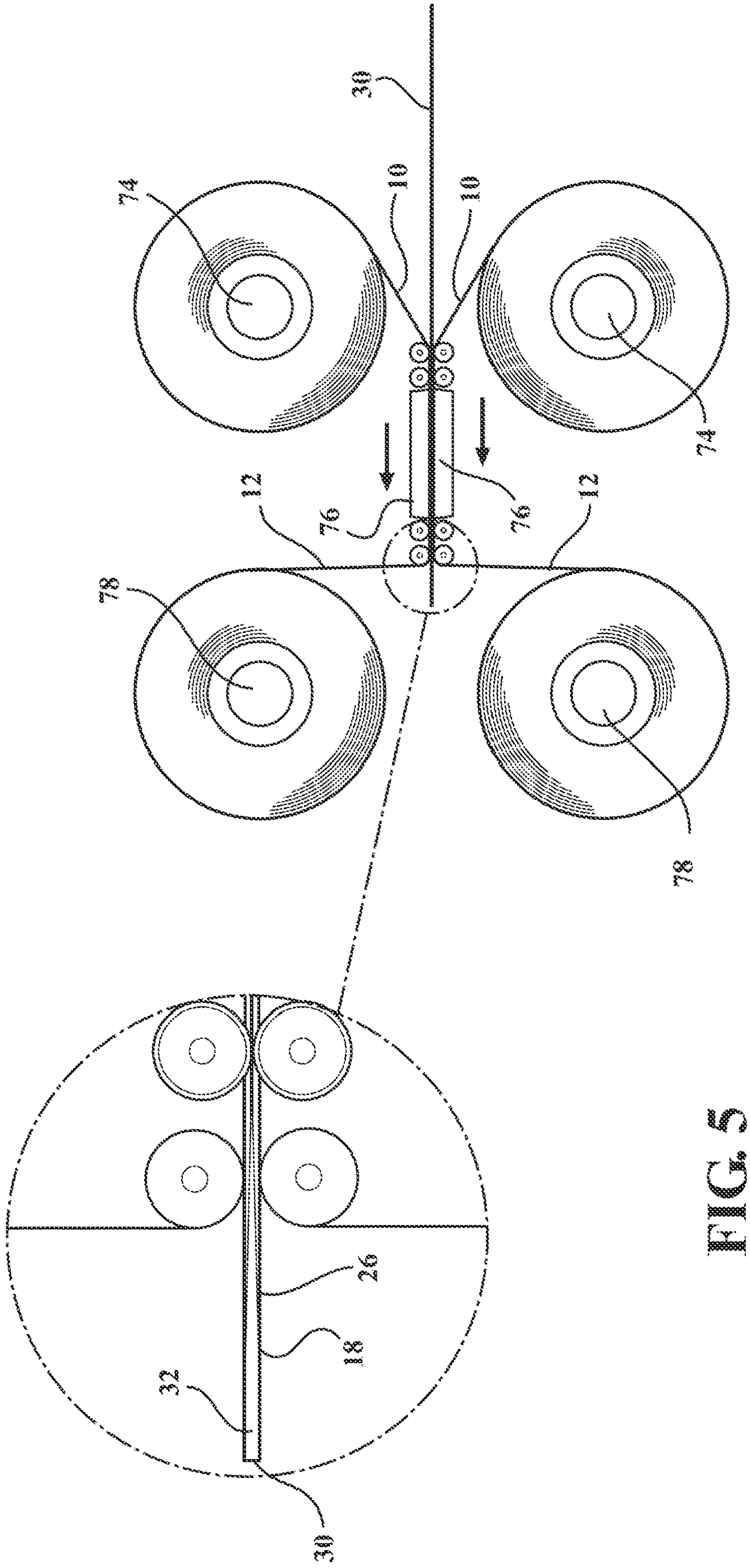
FIG. 5 illustrates a method of applying the tape assembly to the catheter shaft via a heat transfer process.

Once the tape assembly 10 is manufactured and spooled onto a continuous roll, it can then be transferred to the catheter shaft 30 via several ways. As mentioned previously, a preferred method of transferring the circuit assembly 17 to the catheter shaft 30 is via a heat transfer process, such as shown in FIG. 5. As an example of this process, the catheter shaft 30 is inserted into and passed along a conveyor system, while at least one spool 74 of the tape assembly 10 is pressed against the catheter shaft 30 as the catheter shaft 30 advances through a heat station 76. If the adhesive layer 28 is not present, the heat helps to mechanically bond the conductive material of the conductive circuit layer 18 to the thermoplastic material of the catheter shaft 30, while at the same time lowering a force of an adhesive bond between the removable transfer media layer 12 and the conductive circuit layer 18. In other words, heat has two primary functions during transfer of the circuit assembly 17 to the catheter shaft 30. First, the heat lessens the holding force of the conductive circuit layer 18 from the removable transfer media layer 12. Second, if the conductive circuit layer 18 is applied directly to the thermoplastic polymer of the catheter shaft 30, the heat helps to mechanically lock the circuit assembly 17 securely to the catheter shaft 30. After passing through the heating station 76, the removable transfer media layer 12 is then lifted off of the circuit assembly 17 leaving the circuit assembly 17 behind. The removable transfer media layer 12 can be gathered in a release spool 78. If present, the seal layer 29 could make releasing the circuit assembly 17 from the transferable media layer 12 easier since bonding to high energy surfaces such as PeBax creates a lesser bond than when bonded directly to copper, such as present in the preferred composition of the conductive circuit layer 18.

Although described and illustrated as being applied to the outer surface 32 of the catheter shaft 30, inclusion of the adhesive layer 28 allows the circuit assembly 17 to be applied earlier in the smart catheter manufacturing process, such as being applied directly to the braid layer 34, prior to the braid layer 34 being covered with polymer to form the outer surface 32.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A tape assembly for transferring at least one circuit onto a catheter shaft, the tape assembly comprising:

a removable transfer media layer extending between a first end and a second end;

a circuit assembly disposed in overlaying and releasably bonded relationship with said removable transfer media layer between said first and second ends;

said circuit assembly including a conductive circuit layer having at least one circuit and a dielectric layer disposed in overlaying relationship with said conductive circuit layer to dispose said conductive circuit layer in sandwiched relationship between said dielectric layer and said removable transfer media layer;

wherein said removable transfer media layer is removable from said circuit assembly after said circuit assembly is secured to the catheter shaft to leave said dielectric layer facing the catheter shaft and disposed between the catheter shaft and said conductive circuit layer.

2. The tape assembly as set forth in claim 1, wherein said circuit assembly includes an adhesive layer disposed in overlaying relationship with said dielectric layer for use in securing said circuit assembly to the catheter shaft.

3. The tape and transferable circuit assembly as set forth in claim 1, wherein said transferable media layer is a tape.

4. The tape assembly as set forth in claim 3, wherein said tape is a heat transfer tape.

5. The tape assembly as set forth in claim 3, wherein said tape is a heat release tape.

6. The tape assembly as set forth in claim 3, wherein said tape is a low adhesion tape.

7. The tape assembly as set forth in claim 1, wherein said at least one circuit extends between at least one first contact pad disposed adjacent said first end of said removable transfer media layer and at least one second contact pad disposed adjacent said second end of said removable transfer media layer.

8. The tape assembly as set forth in claim 1, wherein said conductive circuit layer and said at least one circuit are comprised of conductive material.

9. The tape assembly as set forth in claim 1, wherein said conductive circuit layer is manufactured via conductive inks.

10. The tape assembly as set forth in claim 1, wherein said conductive circuit layer is manufactured via chemical etching.

11. The tape assembly as set forth in claim 1, wherein said circuit assembly is transferred to the catheter shaft via a heat transfer process.

12. A tape assembly for transferring at least one circuit onto a catheter shaft, the tape assembly comprising:

a removable transfer media layer extending between a first end and a second end;

a circuit assembly disposed in overlaying and releasably bonded relationship with said removable transfer media layer between said first and second ends;

said circuit assembly including a conductive circuit layer having at least one circuit and a seal layer disposed in sandwiched relationship between said transfer media layer and said conductive circuit layer;

wherein said removable transfer media layer is removable from said circuit assembly after said circuit assembly is secured to the catheter shaft to leave said seal layer in overlaying relationship with said conductive circuit layer for protecting said conductive circuit layer from an environment of the catheter shaft after removal of said removable transfer media layer.

* * * * *